United States Patent [19]
Fain et al.

[11] Patent Number: 5,176,135
[45] Date of Patent: Jan. 5, 1993

[54] IMPLANTABLE DEFIBRILLATION ELECTRODE SYSTEM

[75] Inventors: Eric S. Fain, Menlo Park; Thomas J. Fogarty, Palo Alto; Benjamin D. Pless, Menlo Park, all of Calif.

[73] Assignee: Ventritex, Inc., Sunnyvale, Calif.

[21] Appl. No.: 793,325

[22] Filed: Nov. 15, 1991

Related U.S. Application Data

[63] Continuation of Ser. No. 564,676, Aug. 7, 1990, abandoned, which is a continuation of Ser. No. 404,517, Sep. 6, 1989, abandoned.

[51] Int. Cl.⁵ .............................................. A61N 1/372
[52] U.S. Cl. .................................. 128/419 D; 128/786
[58] Field of Search ................... 128/419 D, 783, 784, 128/785, 786

[56] References Cited

U.S. PATENT DOCUMENTS

| | | | |
|---|---|---|---|
| 4,548,203 | 10/1985 | Tacker, Jr. et al. | 128/419 D |
| 4,567,900 | 2/1986 | Moore | 128/419 D |
| 4,708,145 | 11/1987 | Tacker, Jr. et al. | 128/419 D |
| 4,774,952 | 10/1988 | Smits | 128/419 P |

Primary Examiner—Kyle L. Howell
Assistant Examiner—Scott M. Getzow
Attorney, Agent, or Firm—Gerstman & Ellis, Ltd.

[57] ABSTRACT

An electrode system is provided for an implantable cardiac defibrillator. The electrode system includes a first endocardial lead having at least one electrode and a second epicardial or extrapericardial lead with an electrode that has a flexible configuration such that it is able to be straightened or compressed into an introducer but will expand when released from the introducer to provide a substantially larger surface area simulating the surface area of a patch electrode.

3 Claims, 2 Drawing Sheets

IMPLANTABLE DEFIBRILLATION ELECTRODE SYSTEM

This application is a continuation of U.S. application Ser. No. 564,676 now abandoned, filed Aug. 7, 1990 which is a continuation of U.S. application Ser. No. 404,517 now abandoned; filed Sep. 6, 1989 in the name of Eric S. Fain, Thoman J. Fogarty and Benjamin D. Pless for "Implantable Defibrillation Electrode System".

FIELD OF THE INVENTION

The present invention relates generally to the field of implantable defibrillation, and more particularly to implanted defibrillation electrodes that may be used with defibrillators.

1. Background of the Invention

Ventricular tachyarrhythmias are electrical diseases of the heart which may result in "sudden death". In one type, ventricular tachycardia, the heart muscle, which comprises the ventricles, contracts rapidly in a coordinated fashion. In another type, ventricular fibrillation, which may be a sequel to ventricular tachycardia, there is very rapid and uncoordinated contraction of individual muscle fibers of the ventricles. These rapid heart rhythms result in inefficient, or in the case of ventricular fibrillation, no blood being pumped from the heart and will result in death unless an effective intervention is applied within minutes.

It is well known in the field of cardiology that ventricular tachyarrhythmias can be effectively treated by the application of a sufficiently strong electric shock. Such shocks may be delivered manually by medical personnel via electrodes placed outside the body on the chest wall, or directly on the heart during surgery. Recently, implantable defibrillators have been developed which automatically monitor the heart's rhythm and deliver an electric shock via implanted electrodes if a ventricular tachyarrhythmia occurs.

In the past the implanted electrodes designed for use with an automatic implantable defibrillator have consisted of either a superior vena caval catheter electrode coupled with a patch electrode situated near the surface of the heart, or two patch electrodes proximate to the surface of the heart. Because the electrodes are closer to the heart, implanted devices have lower energy requirements than external electrodes for successful termination of ventricular tachyarrhythmias.

Unfortunately, implantation of at least one patch lead requires major surgery, such as a median sternotomy or lateral thoracotomy. Such procedures have inherent risks including hemorrhage, postoperative heart failure, infection, and pneumonia, as well as perioperative mortality. Another disadvantage is that these surgical procedures may exclude patients who are considered to be poor operative risks, but who would otherwise benefit from an implantable defibrillator. For these reasons, a less invasive approach is desirable.

2. Description of the Prior Art

There have been previous attempts to design a less invasive electrode system for use with an implantable defibrillator. One such system involves the use of a single transvenous lead with a distal electrode positioned near the right ventricular apex and a second proximal electrode of opposite polarity positioned in the superior vena cava. The defibrillation shock is then delivered between these two endocardial electrodes. Such 4,355,646; Mirowski et al., U.S. Pat. No. 3,942,536; Speicher et al., U.S. Pat. No. 4,603,705; and Winkle et al., J Am Coll Cardiol 1988; 11:365-70. Although this system is relatively non-invasive, requiring only percutaneous insertion of the catheter, defibrillation efficacy has been shown to be greatly reduced, often having energy/voltage requirements that exceed the maximum output of the currently available implantable defibrillators. This appears to be due to the fact that both electrodes reside in the low resistance blood pool on the right side of the heart, and therefore most of the current does not reach the left ventricle, which represents approximately eighty percent of the heart muscle mass.

Another prior art implantable defibrillation electrode system, Heilman et al., U.S. Pat. No. 4,662,377, consists of pairing a transvenous catheter with a subcutaneous patch electrode positioned over the apex of the left ventricle. While this system has improved efficacy over the right-sided catheter alone, it utilizes one extrathoracic electrode, and therefore has higher energy/voltage requirements than if both electrodes were located close to the heart.

Hielman, U.S. Pat. No. 4,270,549, teaches the use of rectangular paddle electrodes measuring approximately 4×6 cm. The method requires two patches inserted on a detachable mandrel via one or two skin incisions in the abdomen and/or thorax. This still requires up to two skin incisions of sufficient length to insert and maneuver the 4×6 cm patch electrodes. In addition the electrodes in this system may migrate over time. Alternatively, a single unipolar intravascular electrode positioned in the superior vena cava may be substituted for one of the patch leads and paired with a diaphragmatic patch. However, even when the lone patch electrode has a significantly larger surface area than that described in U.S. Pat. No. 4,270,549 and is implanted via a thoracotomy, this lead system has been shown to have decreased efficacy when compared to the commonly used lead system of two patch electrodes situated at the exterior surface of the heart (Troup et al., J Am Coll Cardiol 1985; 6:1315-21).

Another attempted solution is described by Moore, U.S. Pat. No. 4,567,900. The defibrillation lead system consists of a pair of internally deployed electrodes positioned intrapericardially on the epicardial surface of the heart via two delivery catheters. The electrodes in this system may migrate around the surface of the heart over a period of time. If such migration occurs and the two electrodes come into contact, they may create a short circuit and render the system inoperative and damage the defibrillation pulse generator. This may be especially likely, since both electrodes reside within the same restrictive body compartment, the intrapericardial space.

SUMMARY OF THE INVENTION

The present invention provides an implantable electrode system for use with implantable pulse generators, which provide therapy for detected episodes of ventricular tachyarrhythmias by delivering electric shocks through the electrodes.

In accordance with the present invention, an electrode system for an implantable cardiac pulse generator is provided which comprises a first endocardial lead having at least one electrode and a second epicardial or extrapericardial lead having an electrode that has a flexible configuration such that it is able to be straightened or compressed into an introducer but will expand when released from the introducer to provide a substantially larger surface area outside of the introducer. Means are provided for connecting the first and second leads to an implantable cardiac pulse generator.

In the illustrative embodiment, the cardiac pulse generator is a combination defibrillator/pacer. The first lead has an electrode for location within the right ventricle of the heart and is adapted for pacing or sensing, and the first lead also has at least one additional spaced electrode adapted for providing a defibrillation shock.

In the illustrative embodiment, the second lead comprises an epicardial or extrapericardial coil electrode having a peripheral dimension encompassing a shadow area of at least five square centimeters when released from the introducer, so as to simulate a patch electrode.

This novel internal lead system has advantages over the prior art in that major surgery can be avoided during its implantation without losing defibrillation efficacy, since it includes both an endocardial catheter and an electrode proximate to the surface of the heart with a large effective surface area. In addition, since the catheter and coil electrodes do not occupy the same body space, the possibility of a short circuit due to contact secondary to lead migration is eliminated.

A more detailed explanation of the invention is provided in the following description and claims, and is illustrated in the accompanying drawings.

DETAILED DESCRIPTION OF THE PREFERRED EMBODIMENTS

Figure 1:
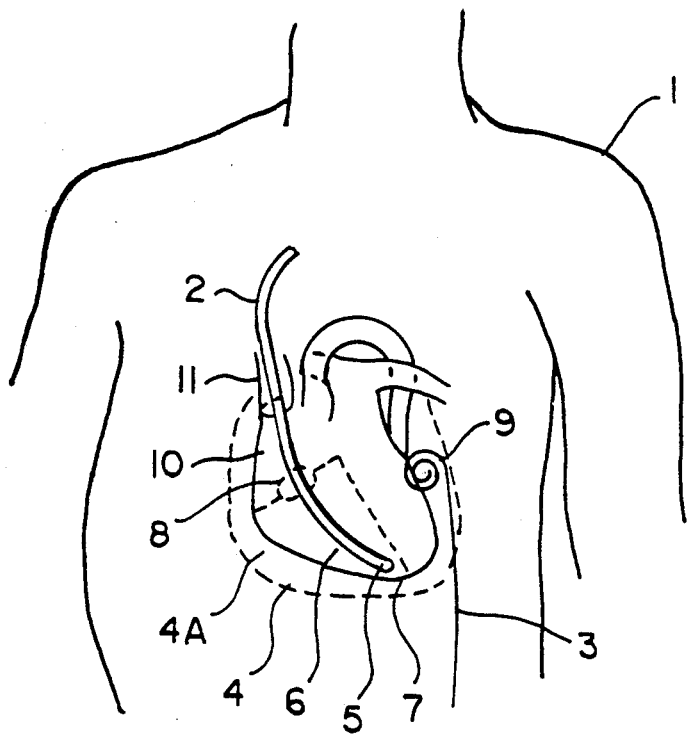
FIG. 1 is a schematic representation showing a defibrillation electrode system constructed in accordance with the present invention, implanted in the body with the coil electrode positioned within the pericardial space.
Figure 2:
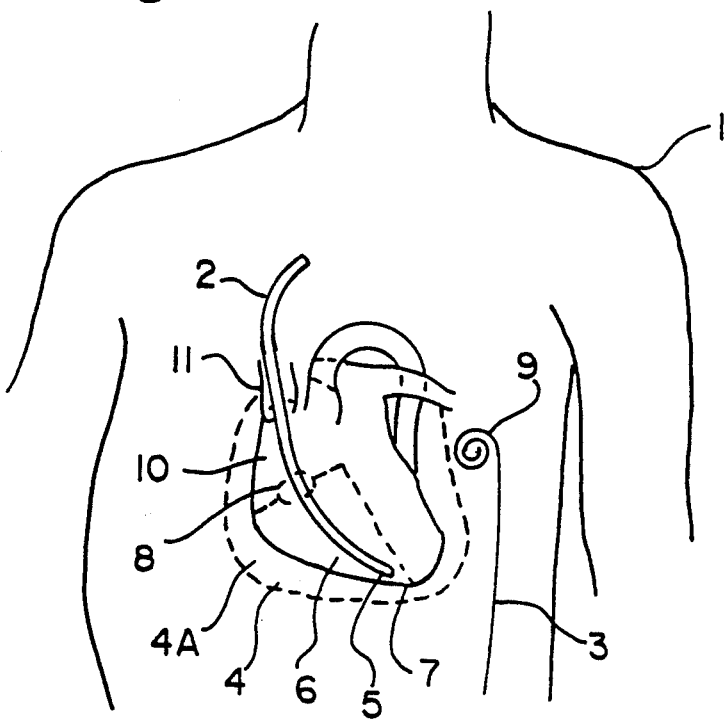
FIG. 2 is a schematic representation showing a defibrillation electrode system constructed in accordance with the present invention, implanted in the body with the coil electrode positioned proximate to the surface of the heart, but outside the pericardium.
Figure 3:
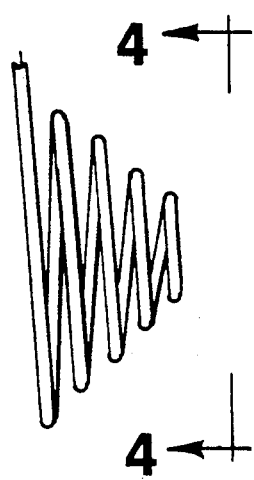
FIG. 3 is a side view of an electrode showing one possible configuration of the coil lead that may be used with the present invention.
Figure 4:
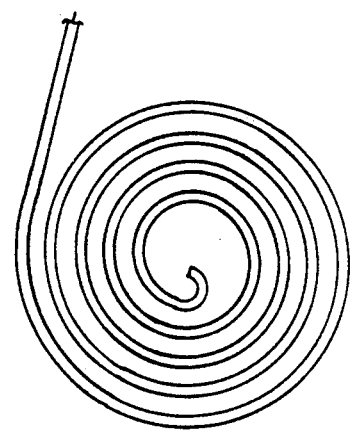
FIG. 4 is a top view of the electrode in FIG. 3.
Figure 5:
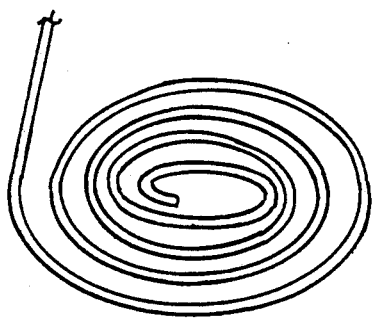
FIG. 5 is a top view of another configuration that can be used with the present invention.
Figure 6:
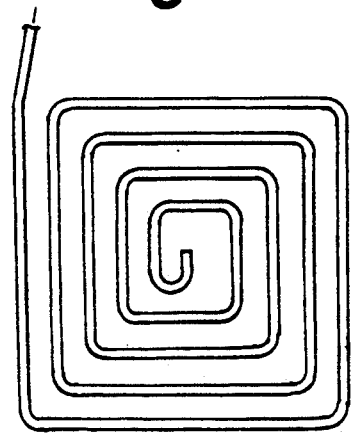
FIG. 6 is a top view of another possible configuration that can be used with the present invention.

FIGS. 1 and 2 illustrate two preferred embodiments of the present invention. One skilled in the art will readily recognize from the following discussion that alternative embodiments of the structure and methods illustrated herein may be employed without departing from the principles of the invention described herein.

An implanted defibrillation electrode system, consisting of a flexible, multi-electrode lead 2 and an internally deployed coil electrode 3, is illustrated in FIGS. 1 and 2. The lead system is designed to be coupled with an implantable defibrillator pulse generator, which has circuitry capable of sensing and detecting tachyarrhythmias and delivering defibrillation shocks via the electrodes. The pulse generator may also include circuitry capable of providing both bradycardia and antitachycardia pacing delivered via the catheter lead. It should be appreciated that, as the term is used herein, defibrillation includes both high and low energy/voltage shocks delivered as therapy for either ventricular tachycardia or ventricular fibrillation.

The electrode 9 at the distal end of the internally deployable coil lead 3 may have various shapes in its deployed state. FIGS. 3 through 6 show examples that may be used. The coil electrode 9 may be implanted within the intrapericardial space 4A, as in FIG. 1, or outside of the pericardium 4 but proximate to the surface of the heart, as in FIG. 2. It may be positioned over the lateral left ventricle, as shown in FIGS. 1 and 2, but may also be placed proximate to the diaphragmatic, posterior or anterior surface of the heart. The coil configuration provides for an epicardial electrode which simulates the function of a standard patch electrode by having an effective surface area approximately equal to the shadow area enclosed by the outermost perimeter of the coil. The shadow area should be at least 5 square centimeters. The coil electrode may be implanted through a single small incision in the upper abdomen or thorax, and placed in its desired location by passing the straightened lead through the incision via a hollow cannulus. The cannulus may be conformed in various shapes as to facilitate the positioning of the lead.

The multi-electrode lead 2 is inserted intravenously and positioned within the right ventricle 6 of the heart, preferably with the distal end 5 at the right ventricular apex 7. The distal end 5 includes an electrode 15 for sensing and pacing the heart and a mechanism for active fixation of the catheter lead. Of course the sensing/pacing electrode may be located within the right ventricle, but other than at the distal end of the lead. In addition to the distal electrode 15, the portion of the lead lying within the right ventricular cavity may contain one or more individual spaced electrodes 19 for delivery of defibrillation shocks. These individual defibrillating electrodes 29 may have the same or different polarity as surface coil electrode.

The portion of lead 2 lying above the tricuspid valve 8 may contain one or more individual electrodes 21 for delivery of defibrillation shocks. These electrodes 21 may be positioned entirely within the right atrium 10, entirely within the superior vena cava 11, or they may lay partially in the right atrium and partially in the superior vena cava. The individual defibrillating electrodes 21 may have the same or different polarity as surface coil electrode 9 or the individual electrodes 19 residing in the right ventricle. Of course the lead 2 may have no electrodes for delivery of defibrillation shocks lying above the tricuspid valve 8.

It can be seen that the present invention provides a novel and improved electrode arrangement for an implantable defibrillator that does not require major surgery for placement of the defibrillation electrodes. It is also seen that the present invention provides an electrode system which has defibrillation efficacy similar to systems that require major surgery.

Still further, the present invention provides an electrode system that eliminates the possibility of a short circuit occurring due to contact of the electrodes secondary to lead migration. The present invention accomplishes this by configuring the electrode system such that the lead and coil electrodes do not occupy the same body space.

Although an illustrative embodiment of the invention has been shown and described, it is to be understood that various modifications and substitutions may be made by those skilled in the art without departing from the novel spirit and scope of the present invention.

What is claimed is:

1. A method for implanting electrodes for use with an implantable defibrillator, without requiring a thoracotomy, which comprises the steps of:

positioning within a chamber of the heart an endocardial lead having at least one electrode;

providing an electrode introducer having there within a second lead with only a single epicardial or extrapericardial electrode that has a flexible configuration such that it is straightened or compressed in the introducer;

locating the introducer adjacent the surface of the heart;

releasing the second lead from the introducer thereby expanding the surface area of the straightened or compressed single epicardial or extrapericardial electrode substantially, whereby the single epicardial or extrapericardial electrode simulates a patch electrode, said release step including the step of locating the single epicardial or extrapericardial electrode at a location on the heart that is segregated from the inside of the heart chamber in which said endocardial lead is positioned or to be positioned, thereby eliminating the problem of lead migration and short circuiting; and connecting the endocardial lead and the second lead to an implantable defibrillator so that the endocardial lead electrode are adapted to provide a defibrillating shock.

2. A method as defined by claim 1, in which the endocardial lead is positioned within the right ventricle.

3. A method as defined by claim 1, in which the endocardial lead has at least one additional spaced electrode and the epicardial or extrapericardial electrode has an effective surface area of at least 5 square centimeters when released from the introducer.

* * * * *